United States Patent [19]

Thompson

[11] Patent Number: 4,623,343
[45] Date of Patent: Nov. 18, 1986

[54] PARENTERAL FLUID ADMINISTRATION APPARATUS AND METHOD

[75] Inventor: Thomas C. Thompson, McKinney, Tex.

[73] Assignee: Quest Medical, Inc., Carrollton, Tex.

[21] Appl. No.: 590,982

[22] Filed: Mar. 19, 1984

[51] Int. Cl.⁴ ............................................. A61B 19/00
[52] U.S. Cl. ................................... 604/405; 604/241; 604/251
[58] Field of Search .............. 604/181, 184, 186, 246, 604/257, 262, 405, 407, 408, 409, 410, 190, 240–241, 251–255; 141/27; 206/438

[56] References Cited

U.S. PATENT DOCUMENTS

| | | |
|---|---|---|
| 701,671 | 6/1902 | Billings . |
| 984,037 | 2/1911 | Sheets . |
| 1,086,976 | 2/1914 | Abramovitz . |
| 1,546,016 | 7/1925 | Eisele ................................ 604/262 |
| 2,473,153 | 6/1949 | Lager ................................. 604/405 |
| 2,656,835 | 10/1953 | Eisenstein ........................ 128/214 |
| 2,668,533 | 2/1954 | Evans ................................ 128/214 |
| 3,380,489 | 4/1968 | Harautuneian .................... 141/27 |
| 3,625,211 | 12/1971 | Butler ................................ 128/214 |
| 3,662,752 | 5/1972 | Yokoyama ........................ 604/405 |
| 3,783,895 | 1/1974 | Weichselbaum .................. 137/588 |
| 3,783,996 | 6/1974 | Gerard .............................. 206/438 |
| 3,797,521 | 3/1974 | King ................................. 137/525.7 |
| 3,881,640 | 5/1975 | Noble ............................... 222/158 |
| 3,938,520 | 2/1976 | Scislowicz ........................ 128/272.3 |
| 3,965,897 | 6/1976 | Lundquist ......................... 604/246 |
| 3,976,068 | 8/1976 | Lundquist ......................... 128/214 |
| 4,005,710 | 2/1977 | Zeddies ............................ 128/214 |
| 4,133,314 | 1/1979 | Bloom .............................. 128/272.3 |
| 4,175,558 | 11/1979 | Hess, III ........................... 128/214 |
| 4,211,588 | 7/1980 | Raines .............................. 156/73.1 |
| 4,253,501 | 3/1981 | Ogle ................................. 141/27 |
| 4,576,594 | 3/1986 | Greenland ........................ 604/251 |

FOREIGN PATENT DOCUMENTS 0460535  5/1928  Fed. Rep. of Germany ...... 604/257

*Primary Examiner*—C. Fred Rosenbaum
*Assistant Examiner*—Gene B. Kartchner
*Attorney, Agent, or Firm*—Roger C. Clapp

[57] ABSTRACT

A parenteral fluid administration system in which a measured medication dose is drawn into a syringe and the syringe is placed into a hangable bag so that its outlet can protrude from an aperture in the bag. A novel connector secures the delivery tubing in communication with the syringe outlet, and provides an air vent extending into the syringe barrel a sufficient distance to prevent venter air bubbles from being drawn out of the syringe outlet.

6 Claims, 3 Drawing Figures

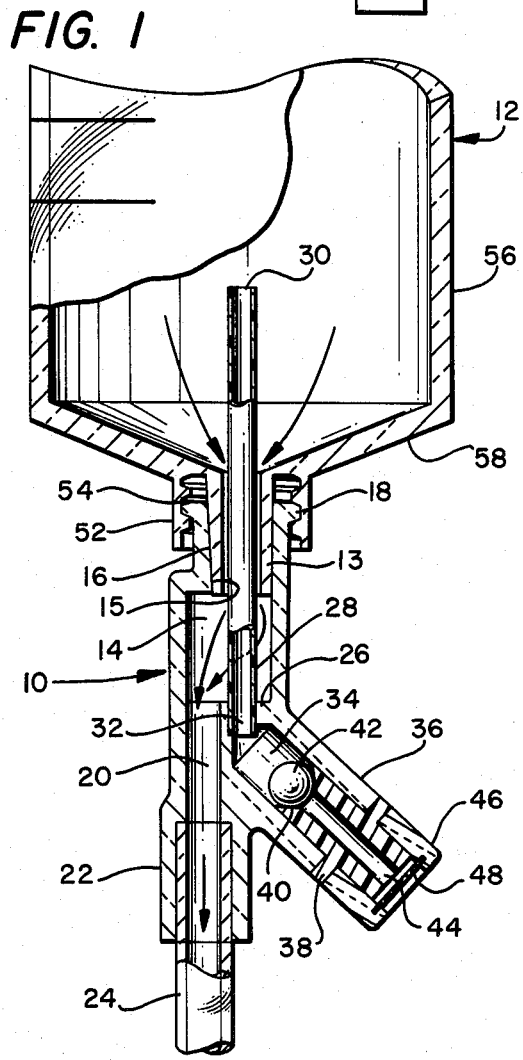
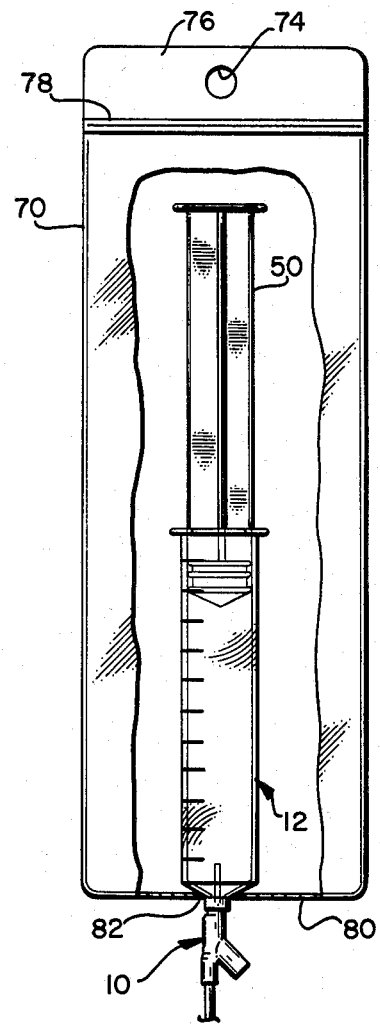

PARENTERAL FLUID ADMINISTRATION APPARATUS AND METHOD

TECHNICAL FIELD

This invention relates to the parenteral administration of fluids, and more particularly to improved apparatus and methods for efficiently, safely and economically delivering measured medication doses to a patient through parenteral administration.

BACKGROUND ART

Parenteral fluids administration is typically accomplished in a hospital following delivery from the hospital pharmacy of the fluids in closed containers. The fluid container may be a relatively rigid one, such as a glass bottle, having a vented closure/connection with an intravenous tube. It may be, as has become more prevalent in recent years, a collapsible container formed from sheets of clear plastic which will collapse as the fluid is delivered.

When a relatively small medication dose is to be delivered as an adjunct to parenteral administration of primary fluids, it may be injected into the patient as a bolus by means of a manually activated syringe. Alternatively, a syringe is deposited in an electronic motor drive for automatically advancing the syringe plunger over a desired period. Most frequently, the dose is delivered over time to the patient from a "mini-bag" which is simply a small collapsible plastic container of the type mentioned above. In that mode of operation, the hospital pharmacy will prepare, measure and transfer the measured medication dose into a mini-bag, utilizing one or more syringes for measurement and transfer. The mini-bag is typically hooked into the intravenous setup by a piggyback arrangement. In the piggyback, a primary fluid line is provided with a check valve and a Y-connector below the valve, and the secondary medication mini-bag is hung higher than the primary fluid container. Such a system is illustrated, for example, in U.S. Pat. No. 4,391,598.

The prevalent practice of mini-bag delivery of medication doses when a gradual infusion is desired requires a substantial materials expense which, in accordance with this invention, can be eliminated. Moreover, this standard practice in the art involves additional manipulation and steps which require, in light of the present invention, unnecessary labor.

SUMMARY OF INVENTION

In accordance with the present invention, there is provided a medication dose delivery system consisting of a flexible plastic bag having a first closable end for receiving a syringe and a second substantially enclosed end having an aperture therein. A disposable plastic syringe containing a measured medication dose is closed into the bag so that the syringe outlet can protrude from the bag aperture in the second bag end. The bag carries means for suspending the bag above the delivery site. The tubing for delivery of fluid to the patient is secured to the syringe by means of a connector which provides an air vent duct extending into the body of the syringe. The syringe, so connected, serves as the medication dose delivery container to deliver the medication without movement of the syringe plunger.

The novel parenteral liquid delivery connector of this invention comprises a hollow body adapted for securement to the outlet of a syringe, a liquid entrance channel extending into the hollow body for communication with the syringe outlet, and a liquid exit port in communication with the entrance channel, and having tubing secured thereto. An air vent duct for passing air from the exterior of the fitting into the syringe extends a sufficient distance into the syringe when the fitting is secured to the syringe so as to prevent air bubbles which are vented at the upper end of the duct from being drawn into the liquid entrance channel of the fitting by flow of liquid from the syringe. The air vent duct is provided with means for preventing the passage of liquid out through the air vent duct.

In a specific embodiment of the connector of this invention, the air vent duct includes a tube of smaller diameter than the liquid entrance channel of the connector body, extending coaxially therewith outwardly from the liquid entrance channel, whereby liquid may flow from the syringe around the outside of the duct into the connector body. The tube extends to a portion of the syringe having a cross-sectional area substantially larger than the cross-sectional area of the outlet. In the preferred embodiment, the proximal end of the duct extends at least as far into the syringe as the substantially constant diameter bore portion of the syringe barrel.

The apparatus of this invention is useful in a new method for preparing and delivering a parenteral medication dose to a patient. The method includes drawing the desired dose into a disposable syringe and depositing the filled syringe into a clear plastic bag having a hole in one end of sufficient size to permit the syringe outlet to protrude. Thereafter, the bag is hung above the patient and a fluid delivery tube is attached to the syringe outlet by means of a connector providing an air vent duct into the body of the syringe, and the distal end of the tube is connected to communicate with a patient catheter site for delivery of the fluid, either through a piggyback setup or other connection.

BRIEF DESCRIPTION OF THE DRAWINGS

A more complete understanding of the invention and its advantages will be apparent from the following detailed description when taken in conjunction with the accompanying drawings, in which:

FIG. 1 is a cross-sectional view of a connector constructed in accordance with this invention attached to a syringe;

FIG. 2 illustrates a loaded syringe enclosed within a bag hanger for use in the practice of the invention; and FIG. 3 is a schematic apparatus of this invention in a typical piggyback administration setup.

DETAILED DESCRIPTION

A parenteral fluids delivery connector 10 is shown in FIG. 1 after its securement to a graduated syringe 12 at syringe outlet 13, for delivery of a measured medication dose from the syringe. The connector 10 is a hollow molded plastic body having a central cavity 14 in communication with an entrance channel 15. Entrance channel 15 is formed at one end of connector 10 and is provided with an internal female luer-taper 16. At the proximal end of the entrance channel 15, luer locking ears 18 are formed.

Fluid exit channel 20 communicates with cavity 14 and extends outward through exit boss 22 carried at the distal end of connector 10. Delivery tubing 24 is bonded to exit channel 20. Delivery tubing 24 serves to provide the channel for delivery of fluids to the patient, and may be provided with such administration set components as needed for the intended use. In practice, connector 10, tubing 24 and such other set components may be supplied in a sterile package to be connected with the syringe at the time the dose is to be administered.

Cavity 14 is provided with a distal shoulder 26 which carries a thin air vent tube 28, which may be formed from metal and insert molded with the connector. Air vent tube 28 extends coaxially with, and outwardly from, entrance channel 15. The upper air venting end of tube 28 must extend into syringe 12. The extent of the protrusion of air vent tube 28 into the syringe body must be sufficient so that air bubbles vented from the venting end 30 are not drawn back down through the syringe outlet 13 by fluid flowing from the syringe. This requires that venting end 30 be positioned above the narrow outlet 13 at a point where the cross-sectional area of the syringe is substantially larger than the outlet area. Air vent channel 32 communicates with air vent tube 28 and extends through shoulder 26 into a valve chamber 34 formed in venting boss 36. A check valve seat member 38 is secured on the end of boss 36, providing a conical valve seat 40 facing chamber 34. A ball 42 is positioned in chamber 34 and is adapted to providing sealing engagement with valve seat 40 to prevent liquid flow from chamber 34. Ball 42 will unseat to permit air to flow into chamber 34 when conditions for liquid flow are established in channel 20. Air entrance channel 44 extends from the valve seat 40 to the end of valve seat member 38, which is secured to the end of venting boss 36. Filter cap 46 covers valve seat member 38, and air filter 48 which covers the path of air through channel 44.

The connector 10 is adapted for cooperation with a standard syringe 12 routinely used in hospitals. Syringe 12 has a plunger 50 for drawing a medication dose in through a male luer-tapered outlet 13. Surrounding outlet 13 is a locking member 52 carrying internal threads 54 for receiving the ears of a female luer-taper fitting. The syringe may in all ways be a standard disposable syringe. It has a main body portion comprising a hollow cylinder 56 of substantially constant diameter. At the distal end of syringe 12, a conical transition section 58 extends between the main body portion 56 and the outlet 13.

Connector 10 is secured to syringe 12 by engagement of the complimentary tapered luer surfaces 16 and 13 of the respective parts, secured in place by turning the connector to interfit the ears 18 with threads 54. When engaged, the air vent 28 extends through outlet 13 well up into the body of the syringe 12, so that its venting end 30 is located in the cylindrical portion 56 of the syringe. Sufficient clearance is left between the outside of tube 28 and the syringe outlet 13 to permit passage of fluid from the syringe into the fitting 10, as generally indicated by the arrows in FIG. 1. For example, a typical minimum inside diameter of outlet 13 is 0.08 inches, and the outside diameter of tube 28 may be 0.05 inches. The ball valve 42 serves to prevent fluid from following any path other than those indicated by the arrows, and specifically to prevent the exit of fluid out the air channel entrance 44. Other means for preventing the passage of fluid through the air vent may be provided. For example, a hydrophobic membrane which will prevent the passage of liquid while permitting the passage of air may be positioned across the air vent path. Other forms of mechanical check valves may be used.

As illustrated in FIG. 2, a convenient means may be provided for handling syringe-measured doses to be used in the system of this invention. A clear plastic bag 70 having an open end 72 for receiving the syringe 12 may be used. Bag 70 is provided with a hole 74 at its upper end 72, as a convenient means for suspending the bag at a desired height. Complementary locking ribs 78 on facing plies of bag 70 adjacent the open end 72 may be pressed to effect bag closure after insertion of the loaded syringe 12. The generally closed end 80 of bag 70 is provided with a small central aperture 82 through which the outlet 13 of syringe 12 may protrude. This permits access to outlet 13 for attachment of connector 10 at the time when the medication dose is to be delivered.

A schematic illustration of a parenteral delivery system with which the invention may be used is shown in FIG. 3. An intravenous pole 90 is provided so that bag 70 may be suspended above the patient. The system illustrated is a piggyback system, wherein the medication dose in syringe 12 is to be delivered into a system through which a primary fluid is being administered. In this setup, the bag 70 is suspended at a higher elevation than the primary fluid container 92. The outlet tubing 24 extending from connector 10 joins the primary fluid delivery tubing 94 at a Y-connector 96. A check valve 98 is provided in line 94 between the principal fluid container 92 and Y connector 96. The common delivery tubing 100 extending from the Y connector 96 is directed to the patient as indicated by arrow 102 through a rate control mechanism 104. Mechanism 104 may be a simple rate-setting roller clamp as used for traditional manual control in parenteral administration sets. In that event, drip chambers may be provided in both lines 24 and 94 to permit observation of the drip rate for manual setting of the clamp.

Preferably, mechanism 104 is a volumetric infusion device such as that illustrated in U.S. Pat. No. 4,391,598, in which event the flow rate is controlled by instrument. Drip chambers are thus not essential. This is particularly so with respect to tube 24 because visual confirmation of flow in that tube will occur by air bubbles arising from the air vent tube 28 in syringe 12.

In this setup, as in all piggyback arrangements, the higher head elevation of the medication dose will cause it to be delivered and check valve 98 to remain closed, until such time as the fluid head in the tubes feeding into Y connector 96 are sufficiently close to permit the check valve 98 to open.

From the foregoing description, it will be appreciated that a very advantageous, simple and economic system for delivery of measured drug doses is possible utilizing the invention. The medication dose may be drawn into the syringe 12 in the step of measuring the dose. Then the filled syringe is closed into bag 70 for delivery to the hospital floor. At the time the drug is to be administered, the set including connector 10 and delivery tubing 24 can be attached to outlet 13 of the syringe 12, primed, and the bag 70 hung so that, upon connection to Y connector 96, the medication dose can be delivered directly from the measuring syringe without movement of the syringe plunger.

Although only one embodiment of the present invention has been illustrated in the accompanying drawing and described in the foregoing detailed description, it will be understood that the invention is not limited to the embodiment disclosed, but is capable of numerous rearrangements, modifications, and substitutions of parts and elements without departing from the scope and spirit of the invention.

I claim:

1. A system for delivering a measured dose of medication comprising:
   a syringe with plunger retracted to define a space containing the desired dose, and having a narrow male luer-tapered outlet;
   a connector having a female luer-tapered inlet secured to the syringe outlet, and carrying an air vent tube extending through the syringe outlet into the interior of the syringe, the air vent tube encompassing a single fluid flow path and being of sufficiently small size to permit liquid to flow out from the syringe into the connector around the outside of the tube.

2. The system of claim 1, wherein one end of the air vent tube extends into the syringe to an area of syringe cross section substantially larger than the cross-sectional area of the outlet.

3. The system of claim 1, in which the connector further comprises means including a ball check valve for preventing passage of liquid out through the air vent tube.

4. The system of claim 1, in which the connector further comprises means including a hydrophobic membrane for preventing passage of liquid out through the air vent tube.

5. A medication dose delivery system comprising:
   a flexible plastic bag having a first, closable end for receiving a syringe and a second substantially closed end having an aperture;
   a disposable plastic syringe having a narrow outlet and containing the medication dose and being closed into the bag with its outlet protruding from said bag aperture;
   means carried by the bag for suspending the bag above the delivery site; and
   delivery tubing secured to the syringe by means of a connector which provides an air vent duct extending into the body of the syringe through the narrow syringe outlet, and permitting liquid flow out from the syringe on the outside of the duct.

6. A method of preparing and delivering a parenteral medication dose to a patient in a hospital comprising:
   drawing a measured dose into a disposable syringe;
   depositing the filled syringe in a bag having a hole in one end of sufficient size to permit the syringe outlet to protrude;
   thereafter hanging the bag containing the syringe above the patient and attaching a fluid delivery tube to the syringe outlet by means of a connector providing an air venting duct into the body of the syringe, whereby the fluid can be delivered from the syringe without movement of the syringe plunger; and
   connecting the distal end of the tube to communicate with a patient catheter site for delivery of the fluid.

* * * * *